(12) United States Patent
Alnajjar et al.

(10) Patent No.: US 11,231,437 B1
(45) Date of Patent: Jan. 25, 2022

(54) ARM MOTION SENSOR SYSTEM

(71) Applicant: UNITED ARAB EMIRATES UNIVERSITY, Al Ain (AE)

(72) Inventors: Fady Alnajjar, Al Ain (AE); Muthanna Ahmed Aziz, Al Ain (AE); Waleed Khalil Ahmed, Al Ain (AE); Munkhjargal Gochoo, Al Ain (AE)

(73) Assignee: UNITED ARAB EMIRATES UNIVERSITY, Al Ain (AE)

( * ) Notice: Subject to any disclaimer, the term of this patent is extended or adjusted under 35 U.S.C. 154(b) by 0 days.

(21) Appl. No.: 17/033,611

(22) Filed: Sep. 25, 2020

(51) Int. Cl.
  *G01P 15/03* (2006.01)
  *A61B 5/11* (2006.01)
  *A61B 5/00* (2006.01)
  *G06N 3/02* (2006.01)

(52) U.S. Cl.
  CPC .......... *G01P 15/032* (2013.01); *A61B 5/0022* (2013.01); *A61B 5/1112* (2013.01); *A61B 5/1123* (2013.01); *G06N 3/02* (2013.01); *A61B 2562/0219* (2013.01)

(58) Field of Classification Search
  CPC .... G01P 15/032; A61B 5/0022; A61B 5/1112; A61B 5/1123; G06N 3/02
  See application file for complete search history.

(56) References Cited

U.S. PATENT DOCUMENTS

| 10,201,202 | B2 * | 2/2019 | Greenly | ............... A61B 5/6826 |
| 2013/0216989 | A1 | 8/2013 | Cuthbert | |
| 2014/0099614 | A1 | 4/2014 | Hu et al. | |

(Continued)

FOREIGN PATENT DOCUMENTS

| CN | 104867309 A | 8/2015 |
| CN | 109589094 A | 4/2019 |
| WO | 2018037318 A1 | 3/2018 |

OTHER PUBLICATIONS

S. I. Lee, J. Daneault, L. Weydert and P. Bonato, "A novel flexible wearable sensor for estimating joint-angles," 2016 IEEE 13th International Conference on Wearable and Implantable Body Sensor Networks (BSN), 2016, pp. 377-382, doi: 10.1109/BSN.2016.7516291. (Year: 2016).*

(Continued)

*Primary Examiner* — Michael J Dalbo
(74) *Attorney, Agent, or Firm* — Nath, Goldberg & Meyer; Richard C. Litman

(57) ABSTRACT

The arm motion sensor system includes at least one sensor attached to the body and positioned to detect arm motions, a control system for detecting when the arm motion is characteristic of a bad habit or activity that may spread infectious disease, and an alert system warning the user to refrain from such activity. In one embodiment, the sensor attached to the wrist and includes a 3-degree of freedom, 9-axis inertial measurement unit and an Edge TPU (Tensor Processing Unit). The wrist sensor communicates with a control system in the Cloud that includes an Artificial Intelligence (AI) unit that is trained to recognize undesirable motions. The wrist sensor includes an alarm system (tactile, auditory, or visual that warns the user to refrain from undesirable arm movements. Optionally, this system may also include an infrared sensor and WiFi MCU (microcontroller unit) positioned near the neck to screen out acceptable arm movements.

6 Claims, 8 Drawing Sheets

(56) References Cited

U.S. PATENT DOCUMENTS

| | | | |
|---|---|---|---|
| 2014/0240103 A1* | 8/2014 | Lake | G06F 3/017 340/12.5 |
| 2014/0335490 A1 | 11/2014 | Baarman et al. | |
| 2015/0313296 A1* | 11/2015 | Hank | A41D 13/0562 2/16 |
| 2016/0198995 A1* | 7/2016 | Yeung | A61B 5/6826 600/595 |
| 2017/0315620 A1* | 11/2017 | Johri | G06F 3/0304 |
| 2018/0292910 A1* | 10/2018 | Valafar | G06K 9/00335 |
| 2020/0079412 A1* | 3/2020 | Ramanathan | G06Q 20/322 |
| 2020/0245900 A1* | 8/2020 | Douglas | A63B 53/00 |

OTHER PUBLICATIONS

Ordonez et al., "Deep Convolutional and LSTM Recurrent Neural Networks for Multimodal Wearable Activity Recognition", Sensors (2016), vol. 16, 115 (25 pages).

Shahmohammadi et al., "Smartwatch Based Activity ecognition Using Active Learning", IEEE/ACM International Conference on Connected Health Applications, Systems and Engineering Technologies (CHASE) (2017), pp. 321-329 (Abstract only).

Pinder et aal., "Digital ehaviour Change Interventions to Break and Form Habits", ACM Transactions on Computer-Human Interaction (2018), vol. 25, Iss. 31 (Abstract only).

* cited by examiner

ARM MOTION SENSOR SYSTEM

BACKGROUND

1. Field

The disclosure of the present patent application relates to motion sensor systems and monitors, and particularly to an arm motion sensor system that may include an alarm or warning system when a person habitually uses his/her arm to engage in a bad habit or in activity that may serve to spread an infectious disease, and in which the system may include artificial intelligence/neural network training to recognize the behavior.

2. Description of the Related Art

According to many studies published in various journals, people touch their faces more than 20 times an hour, on average. About 44 percent of the time, it involves contact with the eyes, nose, or mouth. From picking up objects to turning doorknobs, we're continually touching surfaces contaminated with pathogens. These pathogens can be picked up by our hands and get into the body through mucous membranes on the face eyes, nose, and mouth that act as pathways to the throat and lungs. The coronavirus that causes Covid-19 is believed to be spread mostly by inhaling droplets released when an infected individual coughs or sneezes. But these droplets can also land on surfaces that we touch with our hands. Some pathogens can even last for about nine days on surfaces, so we are constantly coming in contact with potential pathogens that can cause an infection.

All of which explains why it makes sense for health officials to recommend that people try to avoid touching their faces. But as anyone who has consciously attempted to do so knows, it's hard. Unfortunately, touching the face is an act that most people perform without thinking. Whether it is something intrinsic to our species or learned behavior, we continue to repeat it even if we intend to or not. In fact, face touching is a behavior that is triggered by several reasons. While some people do it to express their emotions, others touch their face in a discussion to make a point. Over time, they form a habit that continues to get repeated unless it is consciously broken. It is well known and confirmed that one way to break the cycle is to make it more difficult to touch the face simply, so if people are to wear gloves and glasses, they are less likely to touch their face. Previous outbreaks, such as SARS, have shown the importance of washing hands regularly and not touching the face with them. A study published late last year on hand hygiene and the global spread of disease through air transportation found that if people wash their hands while at the airport, the spread of a pandemic could be curbed by up to 69 percent. The same research group previously found only an estimated 20 percent of people have clean hands while at airports. Moreover, little things really could make a difference in restricting the spread of coronavirus, and an increase in the number of people with clean hands would have a significant impact on slowing it.

So, it is evident that to reduce the infection by Corona, we need to avoid touching our faces. In this direction, we present our devices and methods as an innovative solution trying to overcome this bad habit of touching our faces that eventually will minimize the Corona infection.

Thus, an arm motion sensor system solving the aforementioned problems is desired.

SUMMARY

The arm motion sensor system includes at least one sensor attached to the body and positioned to detect arm motions, a control system for detecting when the arm motion is characteristic of a bad habit or activity that may spread infectious disease, and an alert system warning the user to refrain from such activity. In one embodiment, the sensor attached to the wrist and includes a 3-degree of freedom, 9-axis inertial measurement unit and an Edge TPU (Tensor Processing Unit). The wrist sensor communicates with a control system in the Cloud that includes an Artificial Intelligence (AI) unit that is trained to recognize undesirable motions. The wrist sensor includes an alarm system (tactile, auditory, or visual) that warns the user to refrain from undesirable arm movements. Optionally, this system may also include an infrared sensor and WiFi MCU (microcontroller unit) positioned near the neck to screen out acceptable arm movements.

In another embodiment, the arm motion sensor system has a combination of sensors that may include the wrist sensor (without the TPU), a flexible sensor extending across the elbow that has a Linear Soft Potentiometer (LSP), and at least one infrared proximity sensor for detecting bending movements of the arm. In this embodiment, the control system is a microcontroller with WiFi and Bluetooth Low Energy (BLE) capability. As above, the alarm system may be tactile, auditory, or visual. The system may include a human-machine interface, such as a touchscreen display, for interface with the microcontroller control system.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
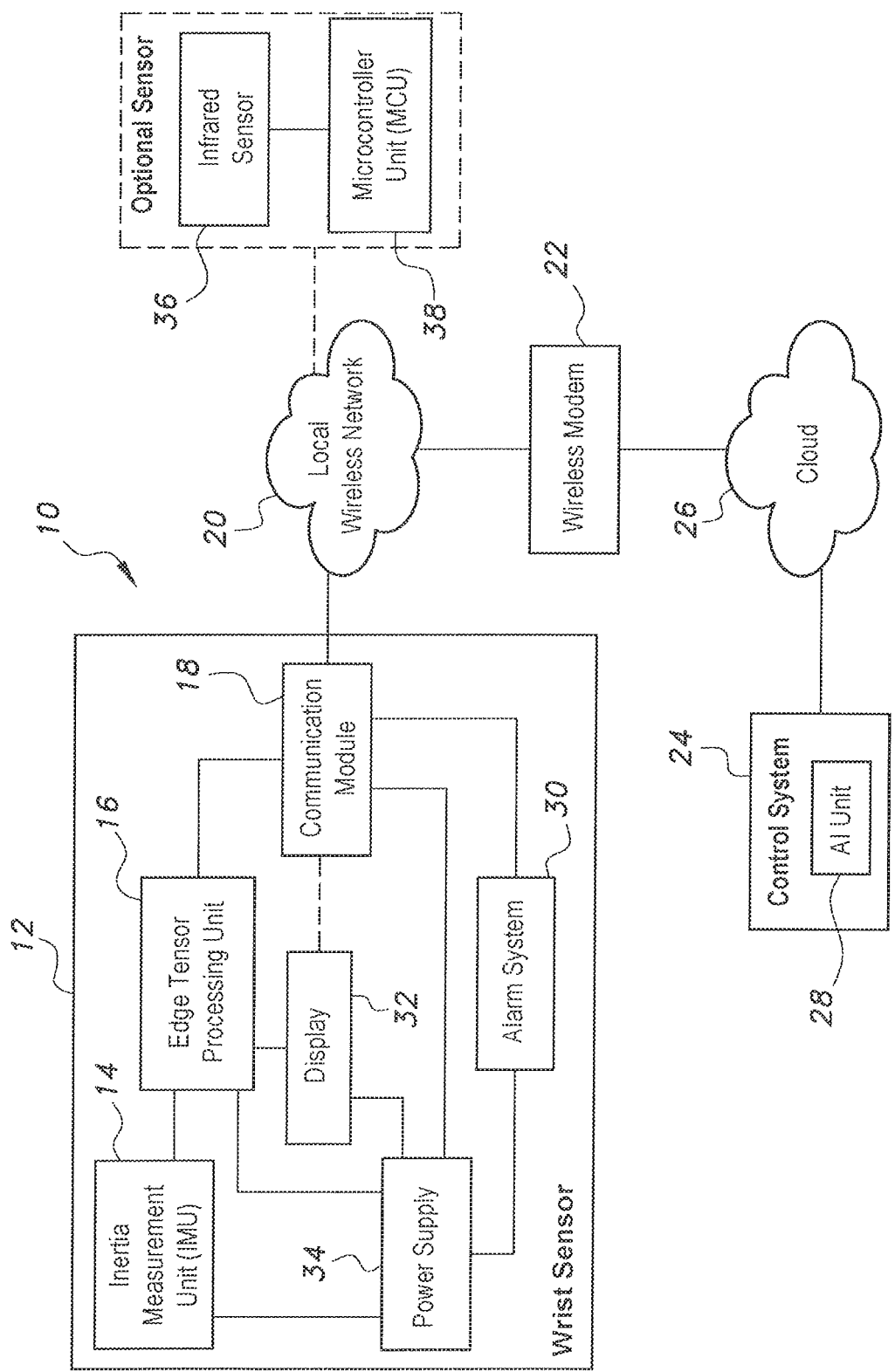
FIG. 1 is a block diagram of a first embodiment of an arm motion sensor system.

The arm motion sensor system includes at least one sensor attached to the body and positioned to detect arm motions, a control system for detecting when the arm motion is characteristic of a bad habit or activity that may spread infectious disease, and an alert system warning the user to refrain from such activity. In one embodiment, the sensor attached to the wrist and includes a 3-degree of freedom, 9-axis inertial measurement unit and an Edge TPU (Tensor Processing Unit). The wrist sensor communicates with a control system in the Cloud that includes an Artificial Intelligence (AI) unit that is trained to recognize undesirable motions. The wrist sensor includes an alarm system (tactile, auditory, or visual) that warns the user to refrain from undesirable arm movements. Optionally, this system may also include an infrared sensor and WiFi MCU (microcontroller unit) positioned near the neck to screen out acceptable arm movements.

In another embodiment, the arm motion sensor system has a combination of sensors that may include the wrist sensor (without the TPU), a flexible sensor extending across the elbow that has a Linear Soft Potentiometer (LSP), and at least one infrared proximity sensor for detecting bending movements of the arm. In this embodiment, the control system is a microcontroller with WiFi and Bluetooth Low Energy (BLE) capability. As above, the alarm system may be tactile, auditory, or visual. The system may include a human-machine interface, such as a touchscreen display, for interface with the microcontroller control system.

In a first embodiment, the system is an AI-based (Artificial Intelligence-based) Upper Limb position recognition system based on machine learning algorithms that can be trained on different positions that are considered as an addictive or nervous habit, and then it can be used to alert and warn the user regarding these habits in order to avoid the habits. The system contains a 9-axis, 3-DOF inertial measurement unit (IMU), which provides real-time 3D-motion profile data analyzed using AI algorithms to detect a variety of Upper Limb positions defined and classified by training as bad habits.

The system can be trained on a variety of addictive or nervous habits that involve using an upper limb, such as kids biting their nails, sucking their thumbs, or touching the nose. In addition, it can be used as an infectious disease control measure to protect against face contamination by touching the face, or any other bad habits in children or adults. The system even can be used to warn the user not to answer his phone while driving. With machine learning capability, the system can recognize a variety of hand positions that can be classified as a good habit or a bad habit. For example, drinking coffee involves moving the hand near the face, but this is considered as a good habit, and the system will not trigger the alarm. Meanwhile, touching the eye with the hand is a bad habit that the system should warn about. In addition, the system provides a personalized experience customized for each user, and the device is trained to recognize these positions, which improves the accuracy and reliability of the device.

For example, classical systems for face contamination prevention by hand touching depend on a sensor that detects only if the hand is near the face based on predefined threshold levels, and it will alert regardless of what the user's intention is. This is a significant reliability issue. In contrast, our system will detect a specific Upper Limb position that has been identified as a bad habit, then raise the alarm. This makes it more reliable, and also more accurate, due to the training process. Moreover, the possibility of training the system on new habits opens the door for new applications.

The system may be composed of two main parts. Part A of the system is the Core system component, viz., a smart wearable device that includes the following. First, a Main Processing unit, which may come in one of two main configurations. The Main Processing unit may include a built-in Edge TPU (Tensor Processing Unit) embedded in the device. This configuration is equipped with built-in edge computing capabilities that enable the device to handle most of the tasks and analysis locally. This improves efficiency by limiting the need for continuous connectivity that sometimes will not be available, besides reducing power requirements. Basically, an Edge TPU is an AI accelerator application specific integrated circuit (ASIC) originally designed by Google that is optimized for Edge computing, i.e., it performs arithmetical operations of the type performed thousands of times by neural networks during training and in application on chip, thereby reducing dependency on the massive computing capabilities available through the cloud and reducing the latency of the resulting network operations.

The other configuration for the Main Processing unit may be a Microcontroller unit (MCU) embedded in the wearable device. This configuration lacks edge computing, making it rely on a mobile application for analysis, and it requires continuous communication with a mobile application. This type of Main Processing unit may be considered a cheaper version of the system.

The Core system components in Part A of the system also include an Inertia Measurement Unit (IMU). A 9-axis, 3-DOF IMU provides real-time 3D-motion profile data analyzed using AI algorithms to detect a variety of hand positions. The system has been implemented and tested using three types of alerting methods. First, by a shock/vibration actuator, second by actuating a buzzer and generating a sound tone, and third by LED's. Finally, the Core system components in Part A of the system include a main display unit as an HMI (human-machine interface) and a battery unit.

Two modes of operations are available. The first is the training mode in which the user is prompted to repeat a certain hand movement several times and classify this as a bad habit. The second is the normal operation mode in which the system will trigger the alarm in case this habit is discovered. Bad habits attempts are logged and counted by the MCU or MPU, and this information is displayed at the display unit. In addition, data stored are communicated wirelessly to a mobile application where historical data are analyzed, and the user can monitor his progress toward reducing such attempts.

Part B of the system is an Optional component that can be affixed near the user's neck. It consists of an infrared sensor and a WIFI MCU. The main purpose of this unit is to detect when the hand will be near the face and send this information to the main processing unit. The purpose of this optional component (when it is activated) is to limit part A from analyzing the hand positions and stay in a sleep mode unless the hand is near the neck. This will help in saving energy and increase battery life by limiting unnecessary complex computations.

In a second embodiment, the system includes a plurality of sensors and a control system operating in stages to reduce power requirements. The system may include the same wrist-mounted sensor including an inertia measurement unit (IMU) providing 9-axis, 3-degree of freedom position sensor measurements, and an arm-mounted sensing unit positioned at the bend of the elbow including a flexible linear soft potentiometer and an infrared sensor for sensing the distance between the forearm and the upper arm when the arm is flexed. The sensors are connected to a microcontroller unit (MCU) programmed to recognize upper arm movements, which may be connected via a WIFI/Bluetooth Low Energy (BLE) module to the cloud and advanced computing resources when needed.

As shown in FIG. 1, the first embodiment of the arm motion sensor system 10 includes a wrist sensor 12 that houses an Inertia Measurement Unit (IMU) 14 connected to an Edge Tensor Processing Unit (TPU) 16. The IMU 14 is a 9-axis, 3-degree of freedom (DOF) sensor providing measurement data forming 3-D position profiles of movement of the arm and hand. Multiple axis, multiple degree of freedom IMUs are commercially available in sophisticate units for complex medical devices to simple plug-in circuit boards for electronics experimenters ad hobbyists, and need not be described further. Measurements from the IMU 14 are provided to the TPU 16, which contains programmable 8-bit parallel arithmetic logic units for performing the thousands of arithmetic calculations required for training and operating neural networks and other artificial intelligence (AI) units, and does so using Edge computing, i.e., locally at the wrist sensor to reduce the amount of data that must be communicated through the Cloud to the AI processing units.

The TPU 16 is connected to a communications module 18, which may include a network interface card (NIC), Bluetooth module, or other interface for communicating data through a local wireless network 20 to a wireless modem 22, which may be a hotspot on a cell telephone or a dedicated router, MiFi, hotspot or the like, for transmission to a control system 24 in the Cloud 26, the control system including an artificial intelligence unit 28 having more powerful processing capabilities than the Edge TPU 16. The communications module 18 also receives control signal responses from the control system 24 and distributes the response accordingly.

The wrist sensor 12 also includes an alarm system 30 that alerts the user when the control system determines that the arm motion represents a bad habit or conduct associated with the spread of infectious disease. The alarm system 30 may be a tactile alarm (a shock or a vibratory motor, similar to vibration of a cell phone), auditory (such as a piezoelectric buzzer), or visual (such as flashing or blinking LEDs). The wrist sensor 12 may also include a display 32, which may be incorporated into the wrist sensor housing or may be a standalone unit connected to the wrist sensor 12 through the communications module 18 and the local wireless network 20. The display 32 may be a touch screen interface, or may be provided by a cell phone, laptop, or other portable device running a software application, and may provide the user with feedback on the number and types of undesirable arm movements and progress in correcting bad habits. Finally, the wrist sensor may include a power supply, 34, which may be a rechargeable battery.

Optionally, the first embodiment of the arm motion sensor system 10 may include an infrared sensor 36 connected to a microcontroller unit 38 that communicates with the AI unit 28 via the local wireless network 20 through the wireless modem 22 to the Cloud 26. The infrared sensor 36 may be positioned, for example, on or near the neck and configured to detect whether the arm motion brings the user's hand close enough to the head or face to engage in undesirable activity. If it does not, the microcontroller unit 38 may signal the AI unit 28, which may send a control signal to the wrist sensor 12 suppressing further calculations until the user's hand nears the face in order to save the power required to perform the thousands of calculations required by the AI algorithms to determine whether the arm motion represents performance of a bad habit.

Figure 2:
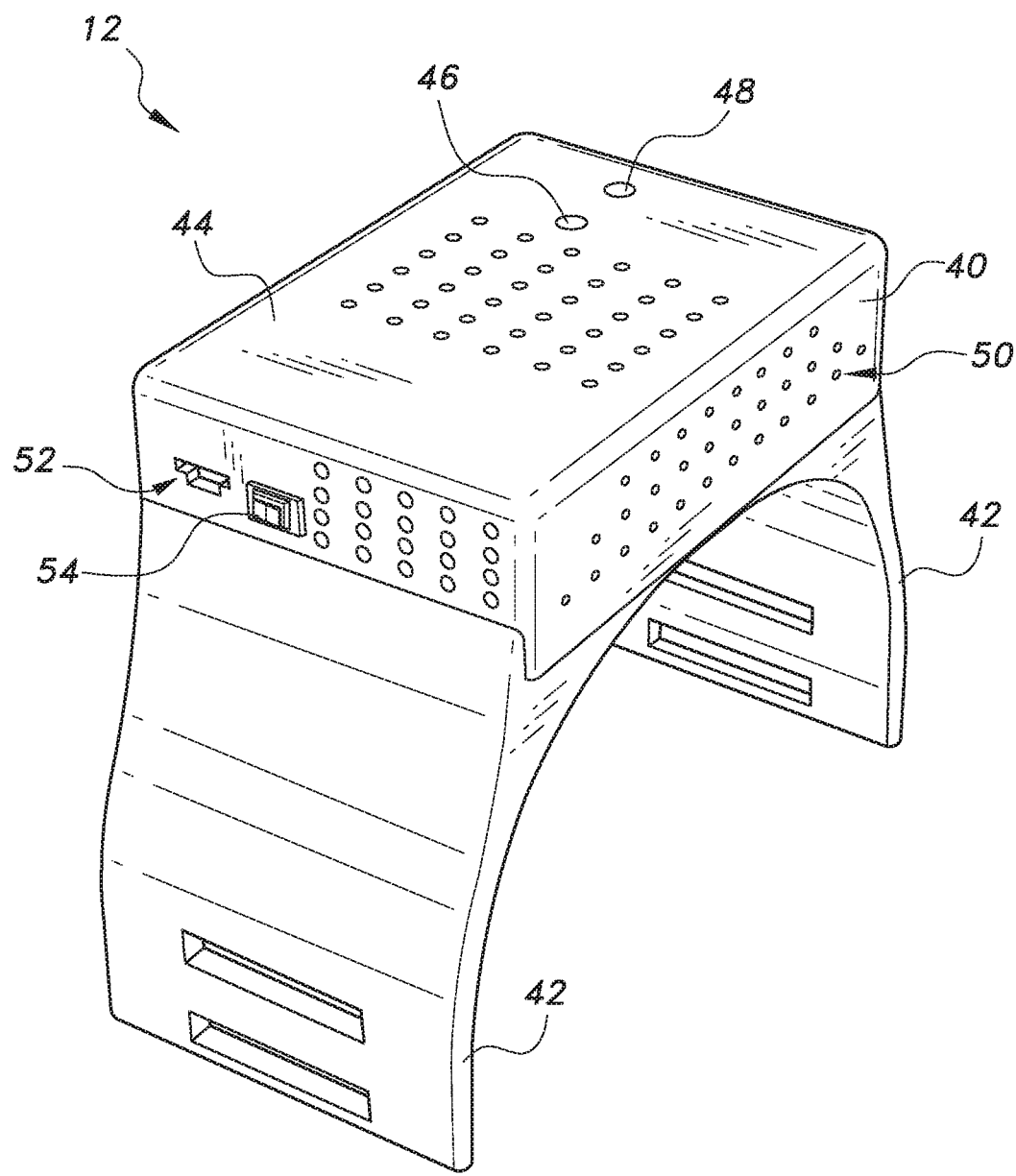
FIG. 2 is a perspective view of a wrist sensor for an arm motion sensor system.

FIG. 2 shows an exemplary wrist sensor 12. The wrist sensor 12 of FIG. 2 has a resilient split band including a central housing 40 having two arcuate clips 42 extending from opposite sides of the central housing 40 for clipping the sensor 12 to the user's wrist. The central housing 40 may have a cover 44 removably disposed over a compartment housing printed circuit boards mounting circuits for the components described above with reference to FIG. 1. he cover 44 may have a display 32 mounted therein, or the display 32 may be provided by a standalone device, as described above. The cover 44 shown in FIG. 2 has a first LED 46 mounted therein as part of the alarm system 30 and a second LED 48 as a power on/off indicator. The cover 44 also has a plurality of ventilation holes 50 defined therein. The side of the central housing 40 also has a charging port 52 mounted therein (the wrist sensor 12 may also have a tag mounted under the central housing 40 for using a wireless battery charger) and an on/off switch 54 mounted therein.

Figure 3:
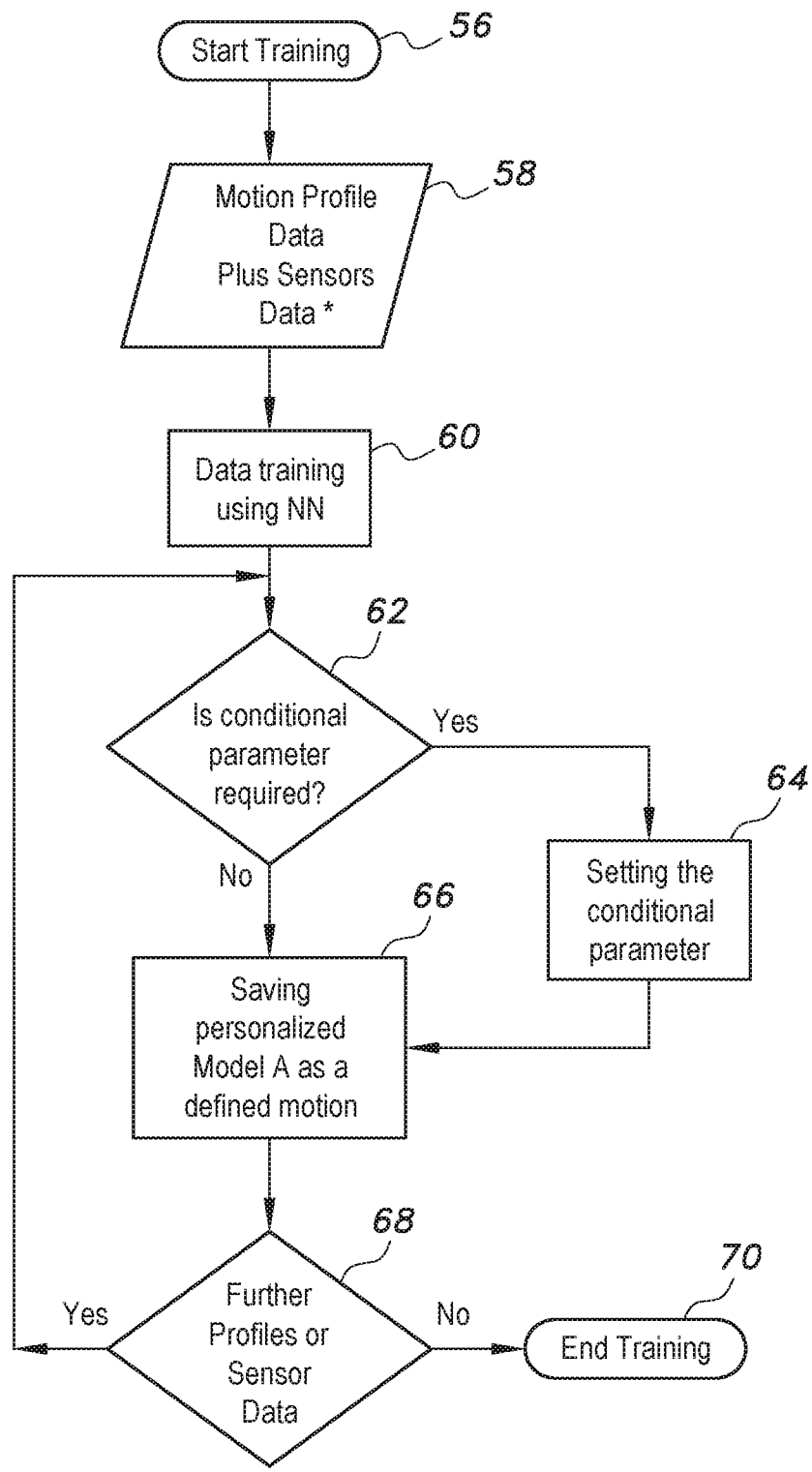
FIG. 3 is a partial flowchart of operation of the first embodiment of the arm motion sensor system in a training mode.

The first embodiment of the arm motion sensor system 10 may operate in one of two different modes, a training mode for training the AI unit, or a normal operating mode. The training mode is performed by having the user repetitively make arm motions characteristic of a bad habit that it is desired to warn the user against making. The wrist sensor 12 collects measurements that are analyzed by the TPU in the first instances to make initial or intermediate calculations, and then sent to the AI unit in the Cloud, which formulates a motion profile characteristic of the bad habit. FIG. 3 shows a partial flowchart of operation in the training mode. The process includes a starting step 56, which involves a step 58 of loading all motion profile data and all sensor data. The process continues with a step 60 of data training using a neural network. In the next step 62, a decision is made whether it is necessary to set a conditional parameter. For example, if the motion profile and sensor data is for a bad habit, such as answering a phone call while driving, then the conditional parameter of acceleration is set at step 64. Otherwise, no conditional parameter need be set for that motion profile and sensor data step, and that combination of sensor data and motion profile may be saved as part of the motion profile at step 66. At step 68, steps 62-66 are repeated for any further motion profiles and sensor data sets being considered. If no further motion profiles or sets of sensor data are left to consider, then the AI training process ends at step 70.

Figure 4:
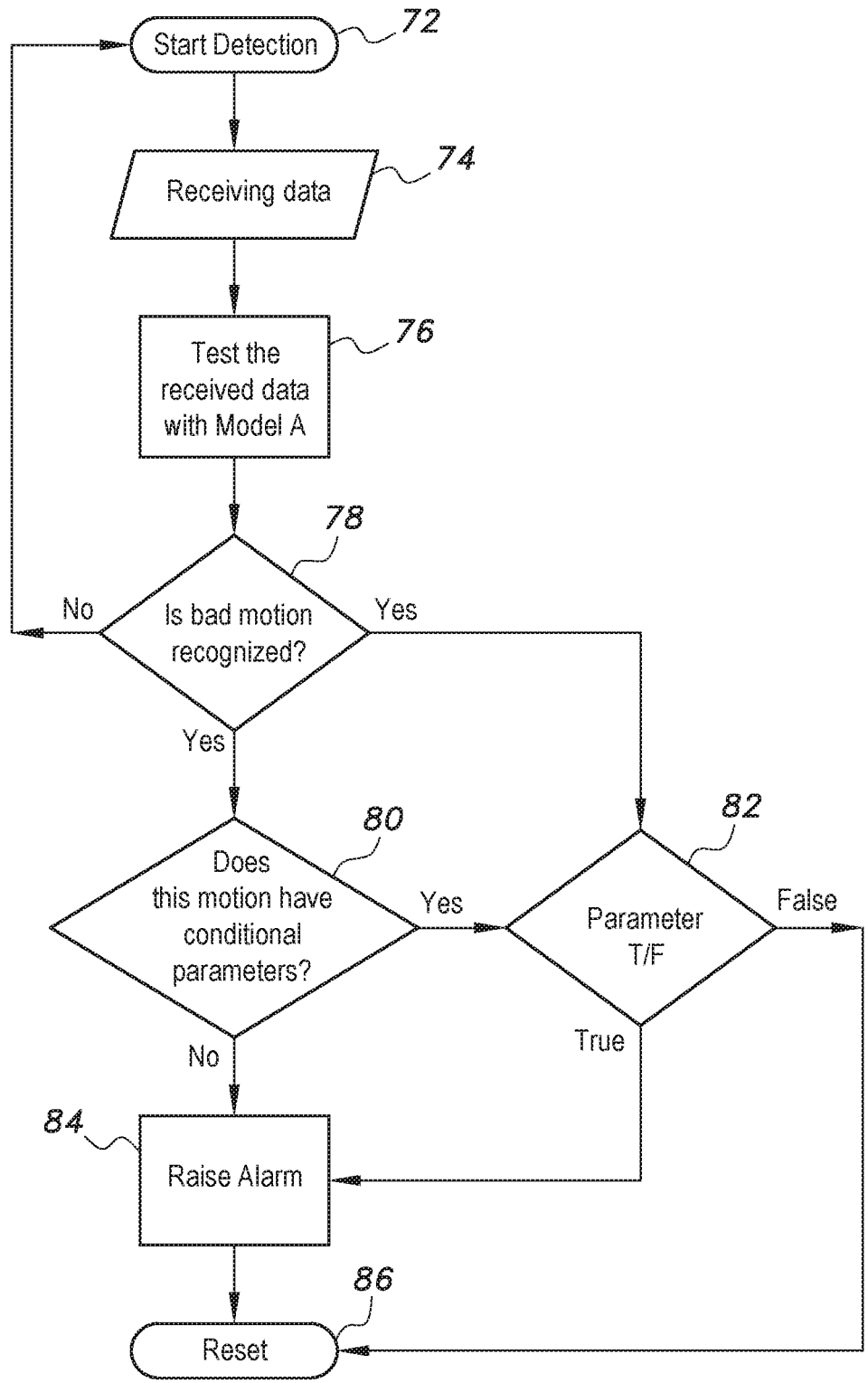
FIG. 4 is a partial flowchart of operation of the first embodiment of the arm motion sensor system in an operating mode.

FIG. 4 shows a partial flowchart of operation in an operating mode. The process includes a starting step 72, which involves a step 74 of receiving data from the wrist sensor 12. At step 76, the sensor data is evaluated in light of the motion profiles established in the training mode, and at step 78, a decision is made whether a bad habit or undesirable arm motion or movement has been detected, and if so, at step 80, whether a conditional parameter has been detected; otherwise, return to the starting step 72 to evaluate additional data. If a conditional parameter is detected at step 82, a control signal is sent to trigger an alarm in the alarm system 30 at step 84. Otherwise, the process is reset at step 86 to receive and evaluate new data.

As noted above, the first embodiment of the arm motion sensor system 10 may lack access to an AI unit 28 in the Cloud 26. Instead, the control system 24 may have a microcontroller unit accessible through the local wireless network 20. In this case, the microcontroller unit would be manually programmed to recognize when the sensor data meets a motion profile and a conditional parameter is detected, and automatically sends a control signal in response triggering an alarm when a bad habit and a conditional parameter is detected. When the system 10 is configured in this manner, the system 10 lacks the advantages of the powerful computing capabilities of AI and may operate more slowly and less accurately, but it is less expensive and may still deliver acceptable performance.

Figure 5:
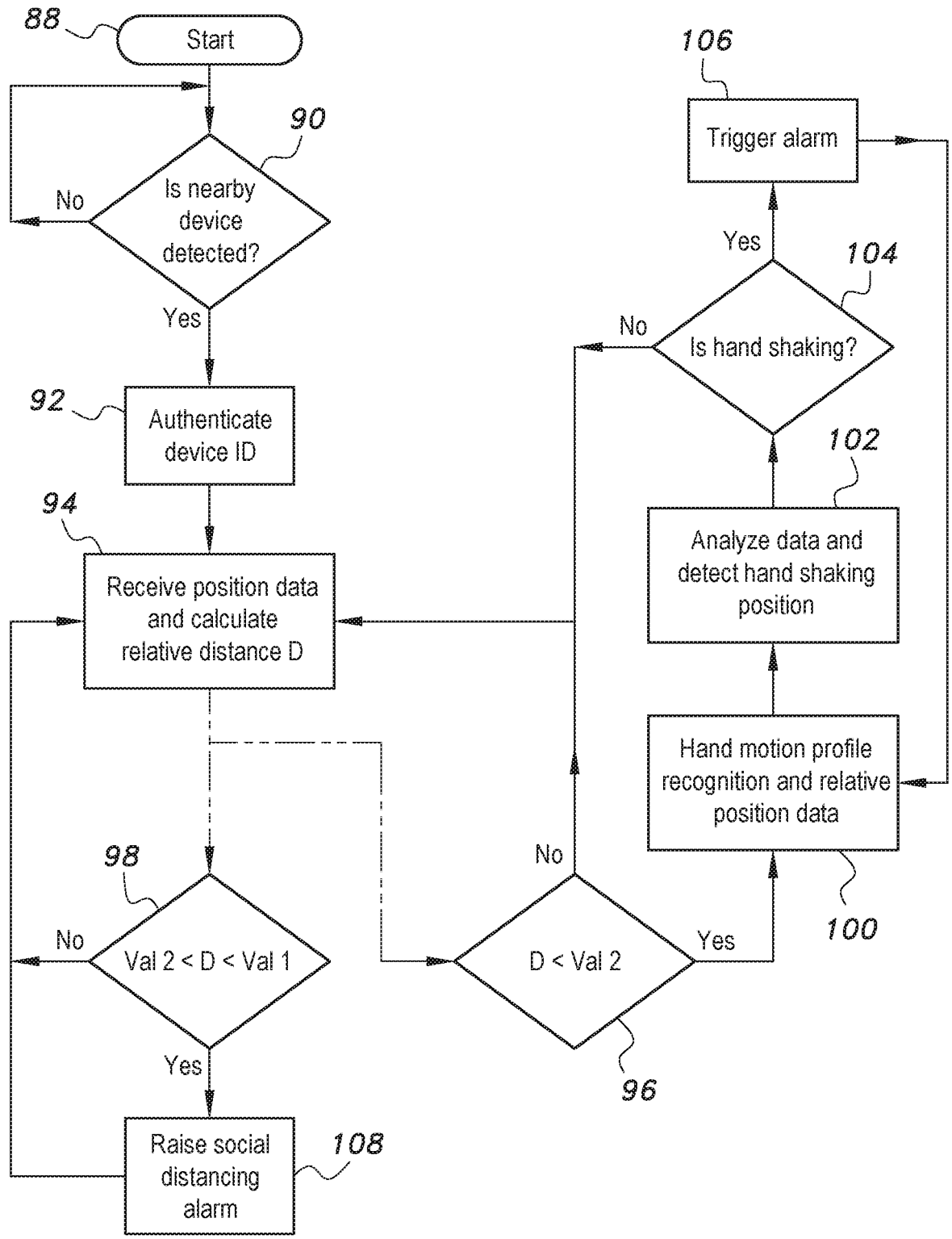
FIG. 5 is a flowchart showing the steps for position identification when the arm motion sensor system is equipped with position sensors for training in social distancing in a group of people.

In times of extraordinary emergency, such as the current coronavirus pandemic generating behavioral response patterns for dealing with COVID-19, the arm motion sensor system 10 may be expanded to include position sensing for training to enforce such measures as social distancing wherever groups of people may collect or congregate. In this case, each wrist sensor 12 may include a Bluetooth Low Energy (BLE) position sensor in the communications module 18 that senses and generates position data when another BLE position sensing module is within range. FIG. 5 is a flowchart showing the steps of operating the system. The process has a starting step 88 that includes a step 90 of continuously monitoring for the presence of a nearby device that is similarly equipped. When such a device is detected, the ID of the nearby device is authenticated at step 92, and position data and the relative distance, D, between the two devices is calculated at step 94. the process then proceeds to simultaneously test whether relative distance D is within a predefined distance (Val 2) indicating the two persons are within handshaking distance at step 96 and whether relative distance D is greater than handshaking distance, but less than a predetermined distance (Val 1) that should not be exceeded for social distancing (Val 2<D<Val 1) at step 98. If at step 96 it is determined that the two persons are within handshaking distance, then the handshaking motion profile and relative position data are loaded at step 100, the data is analyzed to determine if the arm is in handshaking position at step 102, and a determination is made at step 104 whether handshaking is being attempted. If so, a handshaking alarm is triggered at step 106, and the process continually tests until handshaking distance is exceeded. Once handshaking distance is exceeded, the process returns to step 94 to test whether the devices exceed the minimum for social distancing. If at step 98 the devices exceed the minimum for social distancing, a social distancing alarm is triggered at step 108 and the process returns to step 94. Otherwise, the process simply returns to step 94 until either the minimum social distancing is exceeded or the devices are within handshaking distance.

Figure 6:
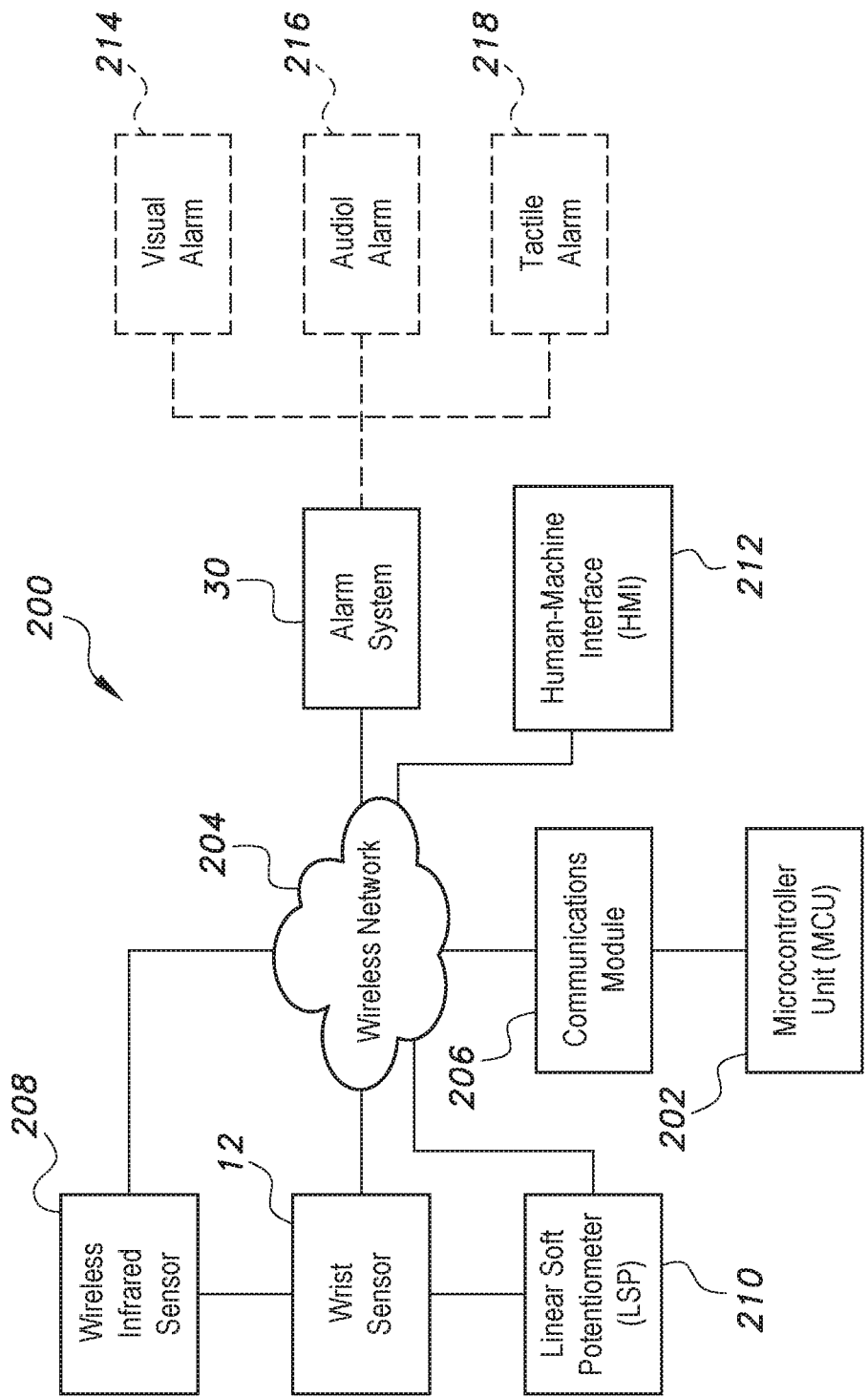
FIG. 6 is a block diagram of a first embodiment of an arm motion sensor system.

As shown in FIG. 6, a second embodiment of the system 200 omits the AI unit accessible through the Cloud, and includes a control system built around a microcontroller unit (MCU) 202 connected to a wireless network 204 via a communications module 206, which may include WiFi and/or Bluetooth. In this embodiment, the system 200 includes a plurality of sensors, including a wireless infrared sensor 208, a wrist sensor 12, and a linear soft potentiometer (LSP) 210, which may be connected to the MCU 202 through the wireless network 204 or by wired connection. The system 200 may include a Human-Machine Interface (HMI) 212, which may be a touch screen monitor or a cell phone or portable computing device, for programming the MCU 202 and receiving the results of calculations for display to the user. The MCU 202 may also be connected to an alarm system 30, which may include a visual alarm 214 for flashing LEDs in a predetermined pattern when a bad habit is detected, an audible alarm 216, such as a buzzer, or a tactile alarm 218, such as a shock or vibration.

Figure 7:
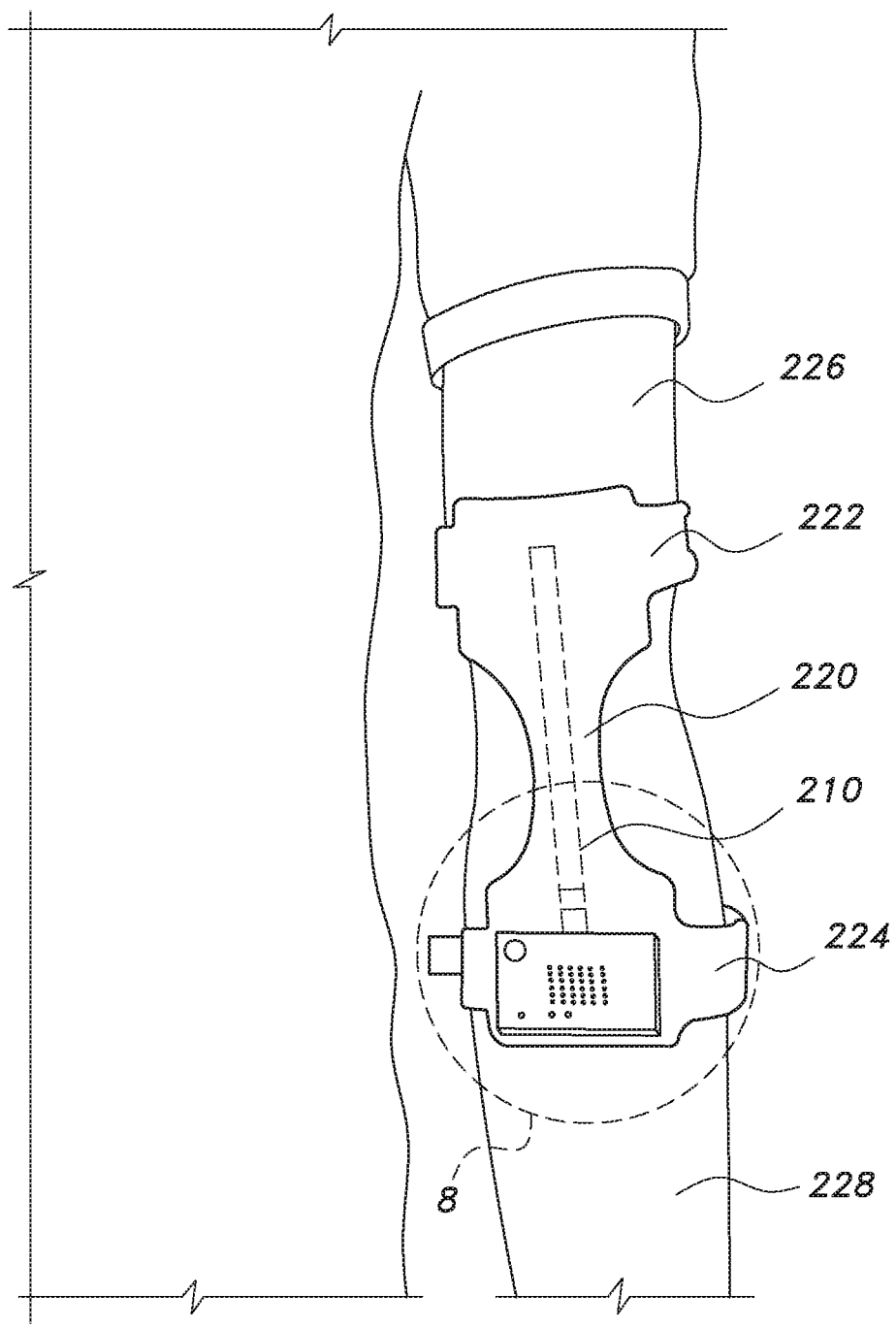
FIG. 7 is an environmental perspective view of a sensor for detecting flexion of the forearm.
Figure 8:
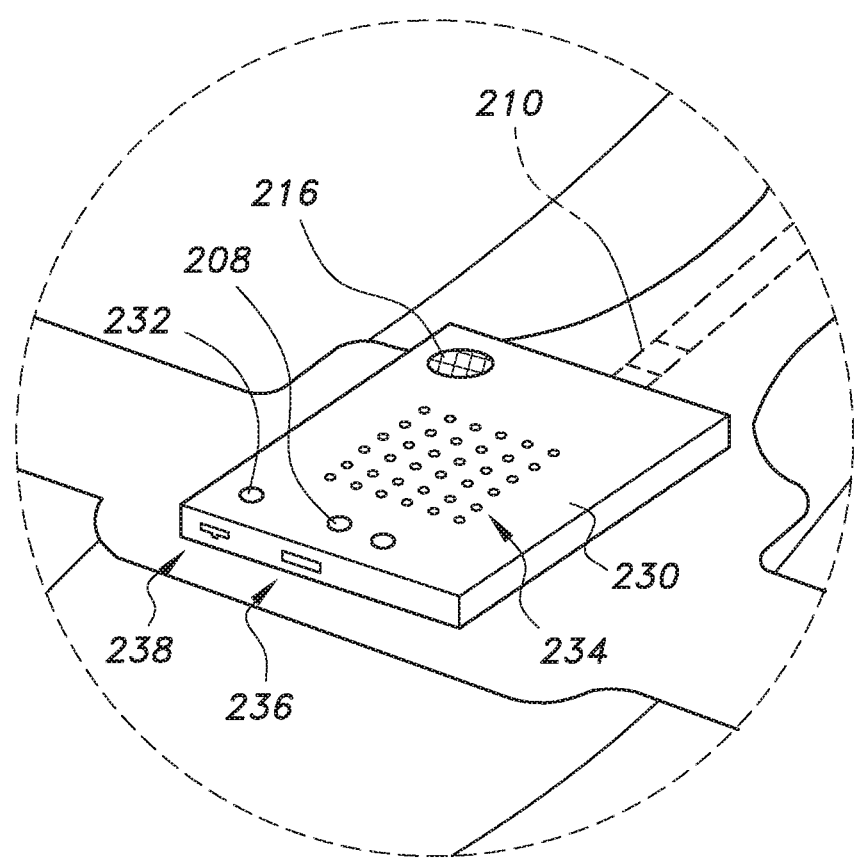
FIG. 8 is a detail view of region 8 of FIG. 7.

As shown in FIGS. 7 and 8, the LSP 210 is a flat, elongated, flexible device that may be attached to a cloth fabric 220 having an upper band 222 and a lower band 224 that may be wrapped around the upper arm 226 and the forearm 228, respectively, and secured to the arm by hook and loop fasteners. The potentiometer 210 itself is an elongated flat strip similar to a ribbon cable having two edge conductors connected to ground and the positive power supply, respectively, and an elongated center conductor that varies in resistance linearly throughout its length so that voltage will vary depending upon where pressure or bending is applied to the center conductor. The LSP 210 may be worn axially parallel to the arm, or transversely across the arm at the elbow, depending upon convenience to the user.

As shown in FIG. 8, the cloth fabric 220 may have a housing 230 attached thereto at one end of the potentiometer 210 that houses circuit boards and related components, and may house the MCU. The housing 230 may have an LED power indicator 232 to indicate when power is applied, the IR sensor 208, a buzzer or audible alarm 216, ventilation holes 234, a USB battery charging port 236 (and also a tag mounted underneath the housing for wireless battery charging), and an on/off switch 238 mounted thereon or defined therein. The housing 230 includes a compartment for storing the battery.

In this embodiment, the arm motion sensor system 200 operates in stages. In the first stage, measurements made by the LSP detect when the arm is making a bending or flexing movement. In the second stage, the IR sensor measures the distance between the upper arm and the forearm. In the third stage, the wrist sensor makes measurements of the 3-D position of the wrist and hand if the measurements by the LSP and the IR sensor indicate the movement is generally indicative of what may be a bad habit.

Similar to the first embodiment, the arm motion sensor system 200 may undergo a training period where the user intentionally makes arm motions characteristic of a bad habit while the sensors make measurements of relative distances and positions. These may be recorded in lookup tables, and the MCU may be manually programmed to recognize a sequence of distances and positions defining a motion profile characteristic of the bad habit, and when a conditional parameter is detected, the MCU may trigger an alarm and store the data in a software monitoring and reporting application. The steps are similar to the flowcharts of FIGS. 3 and 4, but the learning process is performed manually instead of the automatic machine learning provided by artificial intelligence in the first arm motion sensor system 10.

It is to be understood that the arm motion sensor system is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of using an arm motion sensor system for alerting a user to refrain from arm motions indicative of performing a predetermined habit and arm motions indicative of predetermined behavior, comprising the steps of:
   providing the user an arm motion sensor system, the arm motion sensor system comprising:
       a wrist sensor having an inertia measurement unit, the wrist sensor being adapted for attachment to a user's wrist;
       a linear soft potentiometer sensor adapted for attachment to the user's elbow;
       an infrared sensor mounted adjacent the linear soft potentiometer;

a microcontroller unit configured to receive sensor data from the wrist sensor, the linear soft potentiometer, and the infrared sensor; and an alarm system connected to the microcontroller unit, the alarm system having an alarm selected from the group consisting of a visual alarm, an audio alarm, and a tactile alarm, the microcontroller unit configured to evaluate the sensor data received from the sensors and automatically trigger the alarm in response to the sensor data matching a motion profile and conditional parameter to alert the user of arm motions indicative of predetermined behavior movements;

training said microcontroller unit to detect at least one motion profile of a sequence of position data for arm motions indicative of performing the predetermined habit and arm motions indicative of the predetermined behavior, including at least one conditional parameter for triggering an alert to the user;

receiving data at the microcontroller unit from the linear soft potentiometer (LSP);

when the data received from the LSP is consistent with the at least one motion profile, the microcontroller unit comparing data from the infrared sensor with the at least one motion profile;

when the data received from the LSP and the data received from the infrared sensor are both consistent with the at least one motion profile, the microcontroller unit comparing data received from the wrist sensor with the at least one motion profile when from data received from the LSP, the infrared sensor, and the wrist sensor, the microcontroller unit detects the at least one conditional parameter, the microcontroller unit sending a signal to said alarm system triggering the alarm alerting the user of arm motions indicative of performing the predetermined habit or arm motions indicative of the predetermined behavior.

2. The method of using an arm motion sensor system according to claim 1, further comprising a human-machine interface (HMI) connected to said microcontroller unit for programming the microcontroller unit and displaying results to the user.

3. The method of using an arm motion sensor system according to claim 1, wherein said inertia measurement unit comprises a 9-axis, 3-degree of freedom inertia measurement unit for providing 3-D position data of the user's hand to said microcontroller unit.

4. The method of using an arm motion sensor system according to claim 1, wherein said infrared sensor is configured for providing data for relative distance between the user's upper arm and the user's forearm to said microcontroller unit.

5. The method of using an arm motion sensor system according to claim 1, wherein said linear soft potentiometer is positioned to provide data to said microcontroller unit regarding bending and flexion of the user's arm.

6. The method of using an arm motion sensor system according to claim 1, wherein said linear soft potentiometer, said infrared sensor, and said microcontroller unit are incorporated onto an H-shaped mounting unit, the H-shaped unit having first and second opposed horizontal mounting straps and a vertical connecting strap therebetween.

\* \* \* \* \*